US008037052B2

(12) United States Patent
Kariathungal et al.

(10) Patent No.: US 8,037,052 B2
(45) Date of Patent: Oct. 11, 2011

(54) SYSTEMS AND METHODS FOR FREE TEXT SEARCHING OF ELECTRONIC MEDICAL RECORD DATA

(75) Inventors: Murali Kumaran Kariathungal, Hoffman Estates, IL (US); Prakash Mahesh, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 332 days.

(21) Appl. No.: 11/750,819

(22) Filed: May 18, 2007

(65) Prior Publication Data

US 2008/0120296 A1 May 22, 2008

Related U.S. Application Data

(60) Provisional application No. 60/867,039, filed on Nov. 22, 2006.

(51) Int. Cl.
*G06F 17/00* (2006.01)
(52) U.S. Cl. .......................................... 707/709; 707/710
(58) Field of Classification Search .................. 707/1–10, 707/709, 710, 999.001–999.01
See application file for complete search history.

(56) References Cited

U.S. PATENT DOCUMENTS

| 2002/0169793 A1* | 11/2002 | Sweeney | 707/204 |
| 2005/0144162 A1* | 6/2005 | Liang | 707/3 |
| 2007/0061393 A1* | 3/2007 | Moore | 709/201 |

OTHER PUBLICATIONS

Unknown, "Web Crawler", May 21, 2009, Wikipedia, p. 1.*
Perner, Petra, et al., "A Hybrid Tool for Data Mining in Picture Archiving System," Advances in Knowledge Acquisition and Manage, No date available, http://www.springerlink.com/content/fmcre7ygynt1q6b4/.
Monegin, Bernie, "Sifting Mounds of Data," Healthcare IT News, May 1, 2005, http://www.healthcareitnews.com/story.cms?id=2882.
Trevino, Merlina, "Radiology tackles broad range of applications with data mining," PACS Web—Feature, May 26, 2005, http://www.diagnosticimaging.com/pacsweb/printer_friendly/?articleID=163701420.
Author unknown, "Data Mining Tools Boost Radiology Department Productivity" Sep. 26, 2006, http://www.kdnuggets.com/news/2006/n19/37i.html, the full article does not appear to be available.
Dreyer, Dr. Keith J., Clinical Data Mining, Partners Healthcare System, Massachusetts General Hospital, Harvard Medical School, No date available.

* cited by examiner

*Primary Examiner* — Monammad Ali
*Assistant Examiner* — John Hocker
(74) *Attorney, Agent, or Firm* — Hanley, Flight & Zimmerman, LLC

(57) ABSTRACT

Certain embodiments of the present invention provide systems and methods for free text searching of electronic medical records. Certain embodiments provide a system including an interface configured to accept search criteria and display search results and a search engine accepting a free text search query from the interface. The free text search query is based on search criteria entered via the interface. The search engine communicates with a search crawler, which searches electronic medical record data based on the free text search query and provides search results. In certain embodiments, the system may de-identify patient/physician data from the search results. Certain embodiments provide a system for retrieving EMR search results. The system includes an interface configured to accept search criteria and display search results, a database interface adapter for interfacing with an electronic medical record database to transmit and receive data and a formatter for formatting search results.

16 Claims, 7 Drawing Sheets

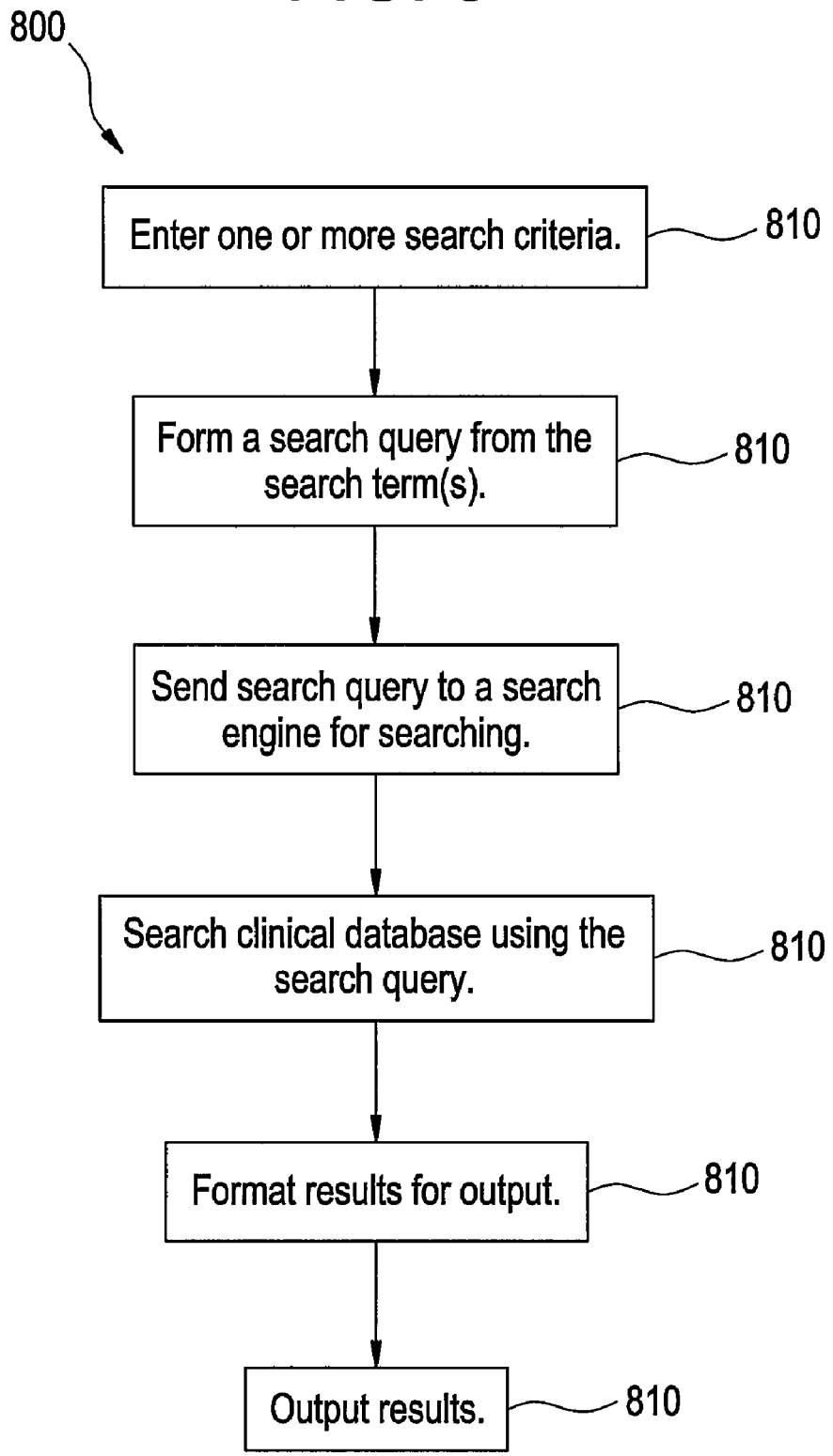

SYSTEMS AND METHODS FOR FREE TEXT SEARCHING OF ELECTRONIC MEDICAL RECORD DATA

RELATED APPLICATIONS

This application claims priority to a provisional application filed on Nov. 22, 2006, as Ser. No. 60/867,039, which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to search and analysis of electronic medical record data. More particularly, the present invention relates to free text searching of electronic medical record data.

Hospitals typically utilize computer systems to manage the various departments within a hospital and data about each patient is collected by a variety of computer systems. For example, a patient may be admitted to the hospital for a Transthoracic Echo (TTE). Information about the patient (e.g., demographics and insurance) could be obtained by the hospital information system (HIS) and stored on a patient record. This information could then be passed to the cardiology department system (commonly known as the cardio vascular information system, or CVIS), for example. Typically the CVIS is a product of one company, while the HIS is the product of another company. As a result, the database between the two may be different. Further, information systems may capture/retain and send different levels of granularity in the data. Once the patient information has been received by the CVIS, the patient may be scheduled for a TTE in the echo lab. Next, the TTE is performed by the sonographer. Images and measurements are taken and sent to the CVIS server. The reading physician (e.g., an echocardiographer) sits down at a review station and pulls the patient's TTE study. The echocardiographer then begins to review the images and measurements and creates a complete medical report on the study. When the echocardiographer completes the medical report, the report is sent to the CVIS server where it is stored and associated with the patient through patient identification data. This completed medical report is an example of the kind of report that could be sent to a data repository for public data mining. Medication instructions, such as documentation and/or prescription, as well as laboratory results and/or vital signs, may also be generated electronically and saved in a data repository.

Today, medical device manufacturers and drug companies face an ever-growing challenge in collecting clinical data on the real-life utilization of their products. As patient medical reports are becoming computerized, the ability to obtain real-life utilization data becomes easier. Further, the data is easier to combine and analyze (e.g., mine) for greater amounts of useful information.

As medical technology becomes more sophisticated, clinical analysis may also become more sophisticated. Increasing amounts of data are generated and archived electronically. With the advent of clinical information systems, a patient's history may be available at a touch of a button. While accessibility of information is advantageous, time is a scarce commodity in a clinical setting. To realize a full benefit of medical technological growth, it would be highly desirable for clinical information to be organized and standardized.

Even if clinical or image-related information is organized, current systems often organize data in a format determined by developers that is unusable by one or more medical practitioners in the field. Additionally, information may be stored in a format that does not lend itself to data retrieval and usage in other contexts. Thus, a need exists to structure data and instructions in a way that is easier to comprehend and utilize.

Data warehousing methods have been used to aggregate, clean, stage, report and analyze patient information derived from medical claims billing and electronic medical records (EMR). Patient data may be extracted from multiple EMR databases located at patient care provider (PCP) sites in geographically dispersed locations, then transported and stored in a centrally located data warehouse. The central data warehouse may be a source of information for population-based profile reports of physician productivity, preventative care, disease-management statistics and research on clinical outcomes. Patient data is sensitive and confidential, and therefore, specific identifying information must be removed prior to transporting it from a PCP site to a central data warehouse. This removal of identifying information must be performed per the federal Health Insurance Portability and Accountability Act (HIPAA) regulations. Any data that is contained in a public database must not reveal the identity of the individual patients whose medical information is contained in the database. Because of this requirement, any information contained on a medical report or record that could aid in tracing back to a particular individual must be removed from the report or record prior to adding the data to a data warehouse for public data mining.

Patient data may be useful to medical advancement, as well as diagnosis and treatment of patients, in a variety of ways. In order to accurately assess the impact of a particular drug or treatment on a patient, for example, it is helpful to analyze all medical reports relating to the particular patient. Removing data that can be used to trace back to an individual patient can make it impossible to group and analyze all medical reports relating to a particular patient. In addition, one of the aims of population analysis is to assemble an at-risk cohort population comprised of individuals who may be candidates for clinical intervention. De-identified data is not very useful to the patient care providers who need to know the identity of their own patients in order to treat them. Users of the system may need the ability to re-identify patients for further follow-up. Portal users may need to re-identify the patients in a process that doesn't involve the portal system, i.e. the process of re-identification occurs on the local user's system.

Increasing numbers of medical information systems require free text search capability for searching finding information about a specific medical diagnosis, patient demographics, decease statistics, etc. Current search engines such as Google, MSN, Yahoo, etc., provide free text search capability with web sites and do not provide such search capability within an enterprise. Additionally, these search engines are not customized for searching electronic medical records.

Therefore, there is a need for systems and methods for free text searching capability with electronic medical records. There is a need for systems and methods for electronic medical record searching in compliance with HIPAA.

BRIEF SUMMARY OF THE INVENTION

Certain embodiments of the present invention provide systems and methods for free text searching of electronic medical records. Certain embodiments provide a system including an interface configured to accept search criteria and display search results. The system also includes a search engine accepting a free text search query from the interface. The free text search query is based on search criteria entered via the interface. The search engine communicates with a search crawler. The system further includes a search crawler searching electronic medical record data based on the free text search query and providing search results. In certain embodiments, the system may include a formatter for formatting the search results for display via the interface. The formatter may de-identify patient and/or physician data from the search results, for example. In certain embodiments, the interface may be a web-based interface, for example. Certain embodiments provide a system of retrieving electronic medical record search results. The system includes an interface configured to accept search criteria and display search results, a database interface adapter for interfacing with an electronic medical record database to transmit and receive data and a formatter for formatting search results.

Certain embodiments provide a method for free text searching of electronic clinical data. The method includes receiving one or more search terms for searching of electronic clinical data. The method also includes forming a search query based on the one or more search terms. The method further includes crawling one or more databases associated with one or more clinical information systems to identify relevant data based on the search query. Additionally, the method includes formatting the relevant data as search results for output.

BRIEF DESCRIPTION OF SEVERAL VIEWS OF THE DRAWINGS

FIG. 8 illustrates a flow diagram for a method for free text searching of electronic clinical data in accordance with an embodiment of the present invention.

Figure 1:
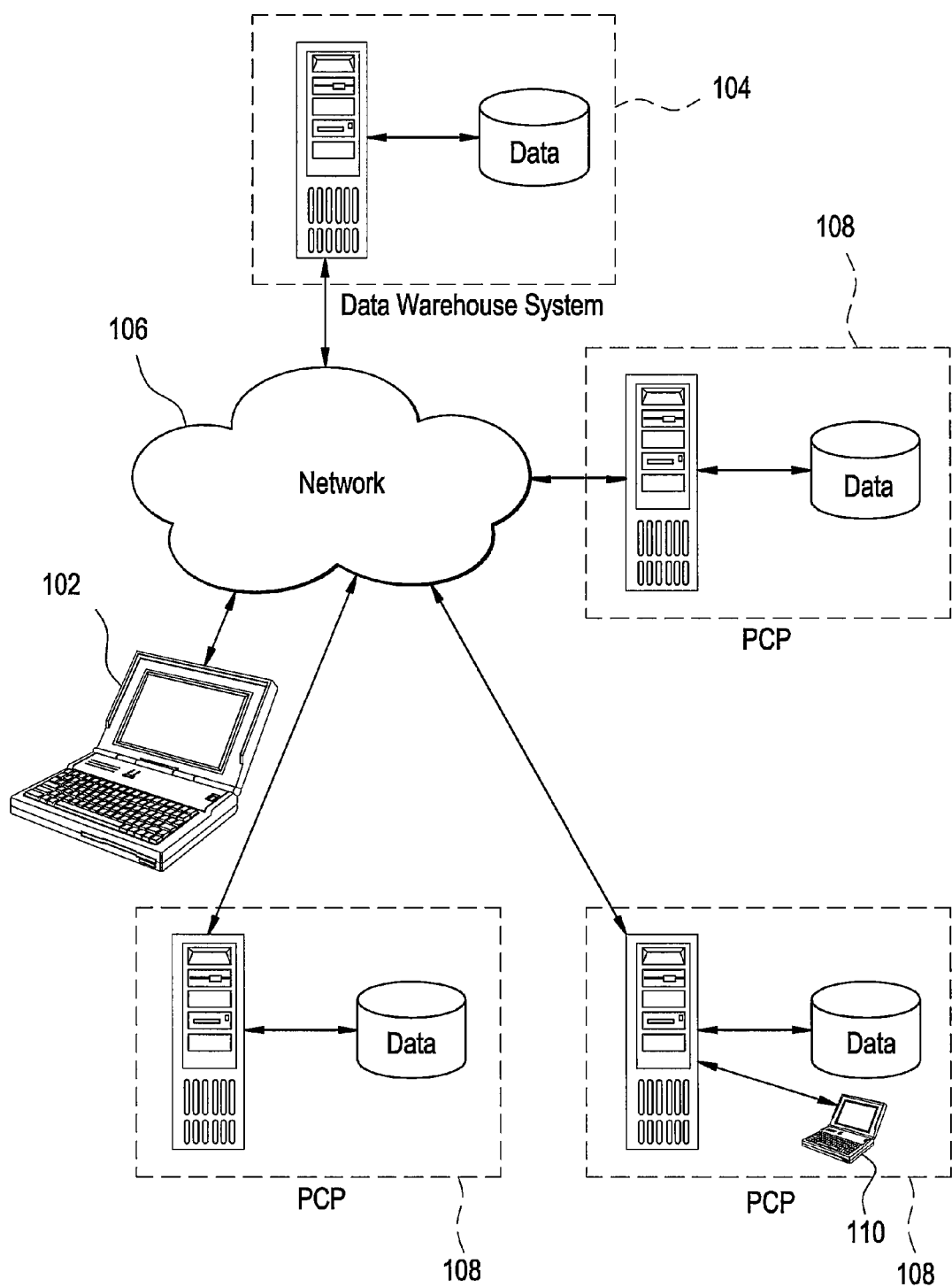
FIG. 1 is an exemplary system for securing patient identity in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide a secure process for sending de-identified patient information from an ambulatory patient care provider (PCP) site to a data warehouse system where the patient data may be analyzed and compared with a wider range of patient data. The terms "de-identified patient information" and "de-identified patient data" as used in this document refer to both fully de-identified data as defined by HIPAA and limited data set data as defined by HIPAA. A limited data set is protected health information for research, public health and health care operations that excludes direct identifiers (e.g., name; postal address other than city, state and zip code; social security number; medical records numbers) but in which other identifying information may remain (e.g., dates of examination; documentation; diagnosis; prescription; lab test results). This is contrasted with fully de-identified data as defined by HIPAA, where all data that may be used to trace back to an individual patient is removed from the record. Information obtained through the data warehouse that pertains to individual patients is transmitted back to the originating PCP site, via a cohort report. Cohort reports are generated by queries that are executed against the data warehouse system to identify patient cohort groups. The individual patients included in a cohort report are then re-identified at the PCP site so that the PCPs may consider the information when deciding on treatment options for the individual patients.

Alternatively and/or in addition, a cohort report may be used to send a list of patients and/or healthcare practitioners qualified for a particular clinical study back to the PCP. For example, a query representing a protocol of a clinical study is packaged and sent to a PCP or other site to be processed by a host EMR application. A report is generated including a set of patients and may alert that one or more patient 'matches' exist.

FIG. 1 is an exemplary system for securing patient identity. PCP systems 108 located at various PCP sites are connected to a network 106. The PCP systems 108 send patient medical data to a data warehouse located on a data warehouse system 104. The PCP systems 108 typically include application software to perform data extraction along with one or more storage device for storing the electronic medical records (EMRs) associated with patients treated at the PCP site. In addition, the PCP systems 108 may include PCP user systems 110 to access the EMR data, to initiate the data extraction and to enter a password string to be used for encrypting a patient identifier. The PCP user systems 110 may be directly attached to the PCP system 108 or they may access the PCP system 108 via the network 106. Each PCP user system 110 may be implemented using a general-purpose computer executing a computer program for carrying out the processes described herein. The PCP user systems 110 may be personal computers or host attached terminals. If the PCP user systems 110 are personal computers, the processing described herein may be shared by a PCP user system 110 and a PCP system 108 by providing an applet to the PCP user system 110. The storage device located at the PCP system 108 may be implemented using a variety of devices for storing electronic information such as a file transfer protocol (FTP) server. It is understood that the storage device may be implemented using memory contained in the PCP system 108 or it may be a separate physical device. The storage device contains a variety of information including an EMR database.

In addition, the system of FIG. 1 includes one or more data warehouse user systems 102 through which an end-user may make a request to an application program on the data warehouse system 104 to access particular records stored in the data warehouse (e.g., to create a cohort report). In an exemplary embodiment of the present invention, end-users may include PCP staff members, pharmaceutical company research team members and personnel from companies that make medical and/or other products. The data warehouse user systems 102 may be directly connected to the data warehouse system 104 or they may be coupled to the data warehouse system 104 via the network 106. Each data warehouse user system 102 may be implemented using a general-purpose computer executing a computer program for carrying out the processes described herein. The data warehouse user systems 102 may be personal computers or host attached terminals. If the data warehouse user systems 102 are personal computers, the processing described herein may be shared by a data warehouse user system 102 and the data warehouse system 104 by providing an applet to the data warehouse user system 102.

The network 106 may be any type of known network including a local area network (LAN), a wide area network (WAN), an intranet, or a global network (e.g., Internet). A data warehouse user system 102 may be coupled to the data warehouse system 104 through multiple networks (e.g., intranet and Internet) so that not all data warehouse user systems 102 are required to be coupled to the data warehouse system 104 through the same network. Similarly, a PCP system 108 may be coupled to the data mining host system 104 through multiple networks (e.g., intranet and Internet) so that not all PCP systems 108 are required to be coupled to the data warehouse system 104 through the same network. One or more of the data warehouse user systems 102, the PCP systems 108 and the data warehouse system 104 may be connected to the network 106 in a wireless fashion and the network 106 may be a wireless network. In an exemplary embodiment, the network 106 is the Internet and each data warehouse user system 102 executes a user interface application to directly connect to the data warehouse system 104. In another embodiment, a data warehouse user system 102 may execute a web browser to contact the data warehouse system 104 through the network 106. Alternatively, a data warehouse user system 102 may be implemented using a device programmed primarily for accessing the network 106 such as WebTV.

The data warehouse system 104 may be implemented using a server operating in response to a computer program stored in a storage medium accessible by the server. The data warehouse system 104 may operate as a network server (often referred to as a web server) to communicate with the data warehouse user systems 102 and the PCP systems 108. The data warehouse system 104 handles sending and receiving information to and from data warehouse user systems 102 and PCP systems 108 and can perform associated tasks. The data warehouse system 104 may also include a firewall to prevent unauthorized access to the data warehouse system 104 and enforce any limitations on authorized access. For instance, an administrator may have access to the entire system and have authority to modify portions of the system and a PCP staff member may only have access to view a subset of the data warehouse records for particular patients. In an exemplary embodiment, the administrator has the ability to add new users, delete users and edit user privileges. The firewall may be implemented using conventional hardware and/or software as is known in the art. In certain embodiments, the data warehouse system 104 is implemented as a plurality of related and/or linked databases or data warehouses.

The data warehouse system 104 also operates as an application server. The data warehouse system 104 executes one or more application programs to provide access to the data repository located on the data warehouse system, as well as application programs to import patient data into a staging area and then into the data warehouse. In addition, the data warehouse system 104 may also execute one or more applications to create patient cohort reports and to send the patient cohort reports to the PCP systems 108. Processing may be shared by the data warehouse user system 102 and the data warehouse system 104 by providing an application (e.g., java applet) to the data warehouse user system 102. Alternatively, the data warehouse user system 102 can include a stand-alone software application for performing a portion of the processing described herein. Similarly, processing may be shared by the PCP system 102 and the data warehouse system 104 by providing an application to the PCP system 102 and alternatively, the PCP system 102 can include a stand-alone software application for performing a portion of the processing described herein. It is understood that separate servers may be used to implement the network server functions and the application server functions. Alternatively, the network server, firewall and the application server can be implemented by a single server executing computer programs to perform the requisite functions.

The storage device located at the data warehouse system 104 may be implemented using a variety of devices for storing electronic information such as a file transfer protocol (FTP) server. It is understood that the storage device may be implemented using memory contained in the data warehouse system 104 or it may be a separate physical device. The storage device contains a variety of information including a data warehouse containing patient medical data from one or more PCPs. The data warehouse system 104 may also operate as a database server and coordinate access to application data including data stored on the storage device. The data warehouse may be physically stored as a single database with access restricted based on user characteristics or it can be physically stored in a variety of databases including portions of the database on the data warehouse user systems 102 or the data warehouse system 104. In an exemplary embodiment, the data repository is implemented using a relational database system and the database system provides different views of the data to different end-users based on end-user characteristics.

Figure 2:
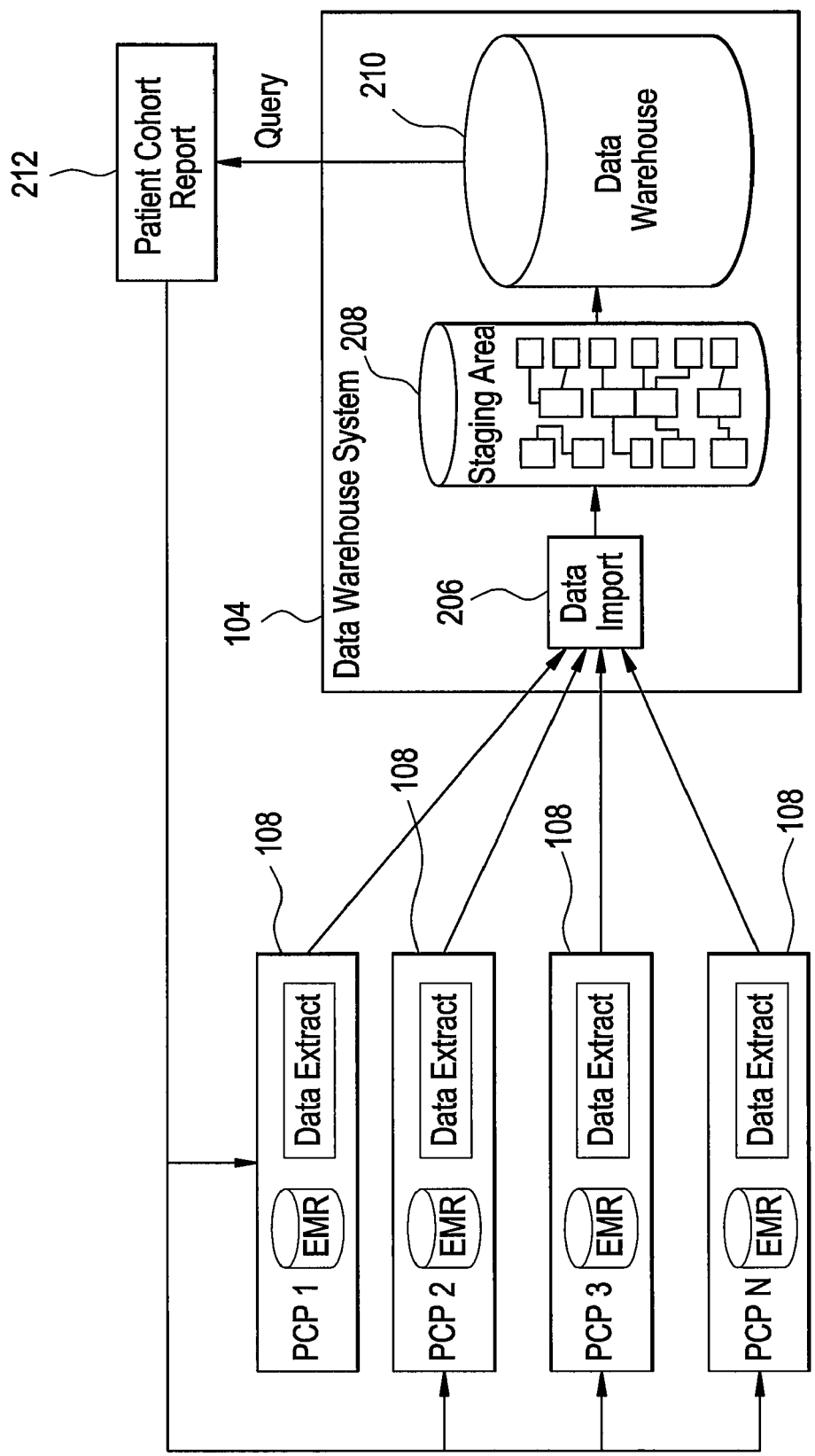
FIG. 2 is a block diagram of an exemplary data warehouse architecture in accordance with an embodiment of the present invention.

FIG. 2 is a block diagram of an exemplary data warehouse architecture. Patient data is extracted from EMR databases located in the PCP systems 108. In an exemplary embodiment of the present invention, an EMR database record includes data such as: patient name and address, medications, allergies, observations, diagnoses, and health insurance information. The PCP systems 108 include application software for extracting patient data from the EMR database. The data is then de-identified and transported (e.g., via Hypertext Transfer Protocol (HTTP) or Secure HTTP (HTTPS)) over the network 106 to the data warehouse system 104. In certain embodiments, the data warehouse system 104 may be implemented as a plurality of data warehouses and/or databases, for example. The data warehouse system 104 includes application software to perform a data import function 206. The data import function 206 aggregates and cleanses de-identified patient data from multiple sites and then stores the data into a staging area 208. Data received from multiple PCP systems 108 is normalized, checked for validity and completeness, and either corrected or flagged as defective. Data from multiple PCP systems 108 is then combined together into a relational database. Aggregation, cleaning and staging data in the described fashion allows the data to be queried meaningfully and efficiently, either as a single entity or specific to each individual PCP site 108. The de-identified patient data is then staged into a data warehouse 210 where it is available for querying.

Patient cohort reports 212 are generated by application software located on the data warehouse system 104 and returned to the PCP systems 108 for use by the primary care providers in treating individual patients. Patient cohort reports 212 may be automatically generated by executing a canned query on a periodic basis. PCP staff members, pharmaceutical company research team members and personnel from companies that make medical and/or other products may each ran patient cohort reports 212. In addition, patient cohort reports 212 may be created by an end-user accessing a data warehouse user system 102 to create custom reports or to initiate the running of canned reports. Further, patient cohort reports 212 may be automatically generated in response to the application software, located on the data warehouse system 104, determining that particular combinations of data for a patient are stored in the data warehouse. An exemplary patient cohort report 212 includes all patients with a particular disease that were treated with a particular medication. Another exemplary patient cohort report 212 includes patients of a particular age and sex who have particular test results. For example, a patient cohort report 212 may list all women with heart disease who are taking a hormone replacement therapy drug. The patient cohort report 212 would list all the patients with records in the data warehouse 210 that fit this criteria along with a warning about the possible side-effects and the likelihood of the side-effects occurring. In an exemplary embodiment, each PCP site receives the entire report, in another embodiment, each PCP site receives the report only for patients that are being treated at the PCP site.

Figure 3:
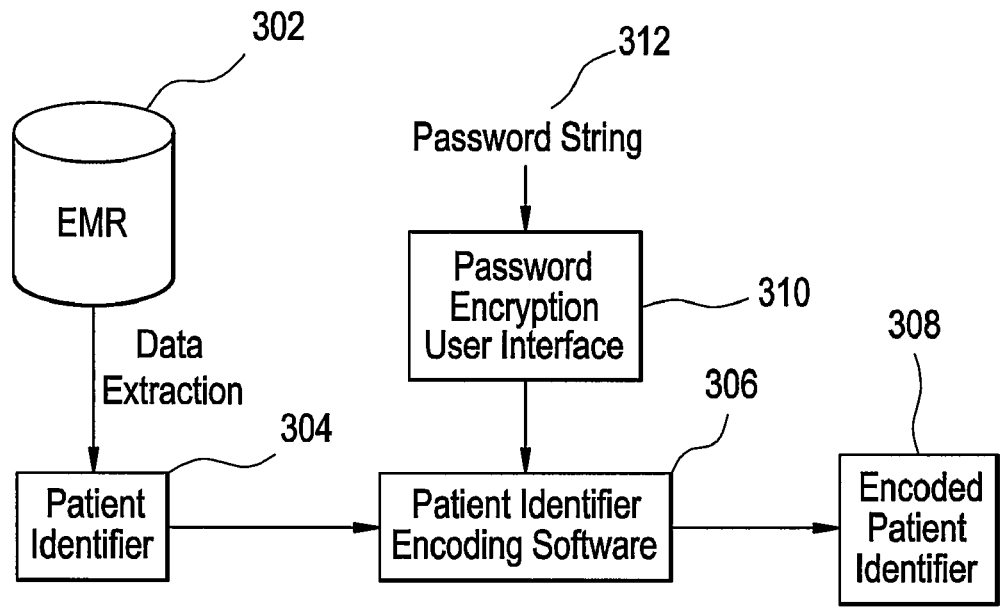
FIG. 3 depicts an exemplary process for de-identifying patient data for storage in a data warehouse used in accordance with an embodiment of the present invention.
Figure 4:
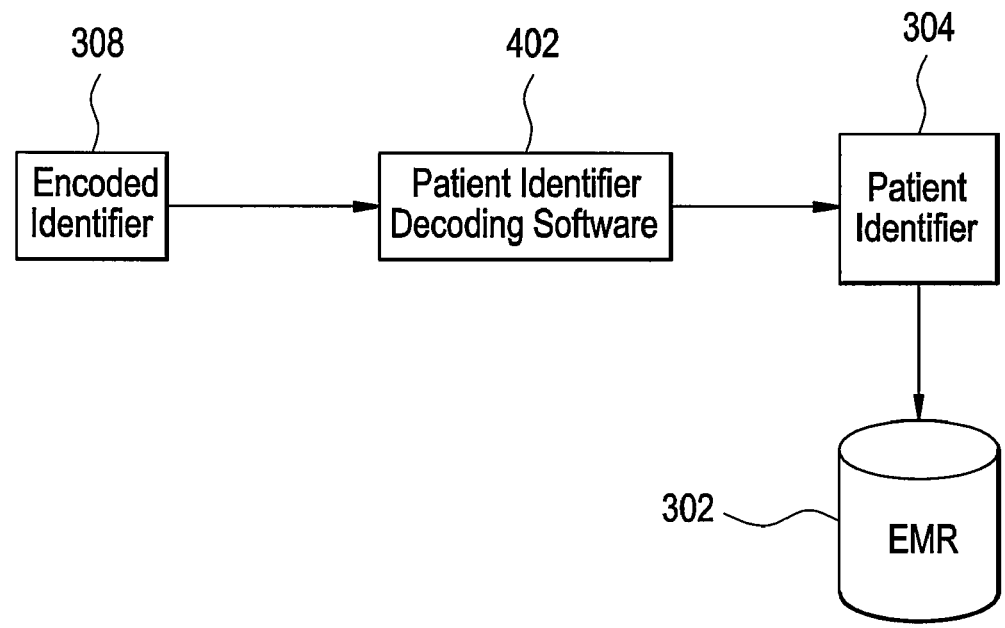
FIG. 4 is a block diagram of an exemplary process for re-identifying a patient from de-identified patient data in accordance with an embodiment of the present invention.

In an exemplary embodiment of the present invention, the ability to create patient cohort reports 212 based on querying longitudinal patient data is supported by the ability to connect all records relating to a single patient in the data warehouse 210. This requires a unique identifier to be associated with each patient record that is transmitted to the data warehouse 210. The unique identifier indicates an anonymous or abstract patient having certain characteristics but does not provide personal direct identifying information such as name, social security number, street address, etc. However, individual PCPs may want to retain the ability to re-identify a patient based on the unique identifier so that the medical personnel located at the PCP site can follow through with the patient in response to information included in the patient cohort reports 212. FIG. 3 depicts an exemplary process for de-identifying patient data for storage in a data warehouse 210 located at the data warehouse system 104 and FIG. 4 depicts an exemplary process for re-identifying a patient from the de-identified patient data contained in a patient cohort report 212.

FIG. 3 is a block diagram of an exemplary process for de-identifying patient data during data extraction for transmission to a data warehouse system 104. The de-identification process removes information that will identify a patient while still retaining clinically useful information about the patient. Patient data is extracted from the EMR database 302 and identifying information is removed, resulting in de-identified patient data. In an exemplary embodiment of the present invention, an EMR database 302 includes the following patient identifying demographic data: names; geographic identifiers, including address; dates directly related to an individual, including birth date, admission date, discharge date and date of death; telephone and fax numbers; electronic mail addresses; social security number; medical record number; health plan beneficiary; account numbers; certificate or license numbers; vehicle identifiers and serial numbers including license plate numbers; device identifiers and serial numbers, web Universal Resource Locators (URLs) and internet protocol (IP) address numbers; biometric identifiers, including finger and voice prints; full face photographic images and comparable images; other unique identifying numbers, characteristics and codes assigned by the PCP or by the EMR system for administrative purposes, including a patient identifier (PID) 304. The EMR database 302 also includes information about: the patient diagnosis or problem; medications taken or prescribed; observations, diagnostic laboratory tests and vital signs; subjective and objective findings, assessments, orders, plans, and notes documented by healthcare providers. The EMR database 302 also includes audit information that records the date, time, and identity of persons who have created, read, updated, or deleted information from the patient record. The EMR database 302 record for each patient also contains a numeric key known as the PID 304 which may be used to uniquely identify an individual patient. The PID 304 is encoded as part of the de-identification process to create an encoded patient identifier (EPID) 308. The EPID 308 is sent, along with the de-identified patient data, to the data warehouse system 104.

The extraction process is performed by application software located on the PCP system 108 and may be executed in the background on a periodic basis (e.g., at 2 a.m. every night, at 2 a.m. every Saturday). In this manner, the extraction process will be less likely to interfere with existing software located on the PCP system 108. The extraction process may also be initiated by a remote system (e.g., the data warehouse system 104) and may include full or incremental back-up schemes. In an exemplary embodiment of the present invention, the following identifiers are removed or transformed in order to create de-identified data that would be classified under the HIPAA definition as fully de-identified data: name, geographic subdivisions smaller than a state including street address, city, county, precinct, zip code (down to the last three digits), dates directly related to an individual (e.g., birth date), phone and fax numbers, electronic mail addresses, health plan number, account number, certificate/license number, device identifier and serial numbers, unified resource locator (URL), internet protocol (IP) address, biometric identifiers, full face photograph, and other unique identifying numbers, characteristics or codes.

In an alternate exemplary embodiment of the present invention, the following identifiers are removed or transformed in order to create de-identified data that would be classified under the HIPAA definition as limited data set information: direct identifiers such as name, postal address (other than city, state and zip code), social security number and medical records numbers. In the limited data set information implementation of the present invention some identifying information may remain such as dates of examination, documentation, diagnosis, prescription and lab test results.

A novel EPID 308 is assigned to each patient based on the PID 304 associated with the patient and a password entered by the PCP. The PID 304 to EPID 308 mapping is not maintained persistently. As depicted in the exemplary embodiment shown in FIG. 3, a password string 312 is supplied by the PCP via a password encryption user interface 310 on the PCP user system 110. This password string 312 is known only to the PCP and is required in order to decode the EPID 308 into a PID 304. The user at the PCP site must have the password string 312 to obtain the PID 304 and this password string 312 must be re-entered each time a patient is to be re-identified. The password encryption user interface 310 may be a graphical user interface. In an exemplary embodiment of the present invention, the user entered password string 312 is encoded using the two-fish algorithm. The two-fish algorithm, as known in the art, is a secret-key block cipher cryptography algorithm that is designed to be highly secure and highly flexible. It utilizes a single key for both encryption and decryption and is often referred to as symmetric encryption.

The encoding is performed by patient identifier encoding software 306 located on the PCP system 108. The patient identifier encoding software 306 also hashes the encoded password string to produce a sixteen-digit number. This sixteen-digit number is numerically added to the PID 304 to create the EPID 308. Other methods of creating the EPID 308 from the PID 304 may be utilized with an exemplary embodiment of the present invention (e.g. Rivest, Shamir and Adelman, RSA, algorithm based on patient name, age and social security number, etc.) as long as the EPID may only be decoded at the PCP site.

FIG. 4 is a block diagram of an exemplary process for re-identifying a patient from de-identified patient data. As described previously, population cohort reports 212 of at-risk patients are created by running queries against the data warehouse 210. De-identified individuals may be tracked longitudinally and queried as members of anonymous population cohorts, based on clinical selection criteria. The query result, contained in the cohort report 212, is a list of EPIDs 308. A list of patient EPIDs 308 in a patient cohort report 212 are received by the PCP system 108. The EPIDs 308 are read into the patient identifier decoding software 402, located on the PCP system 108, and the original PID 304 is recreated or otherwise re-associated with a patient record at the PCP system 108. The PID 304 may be used as a key to look up additional identifying information from the EMR database 302. Employees of the PCP may utilize the patient-specific information from the EMR database 302 to counsel the patient and to decide on treatment alternatives.

An embodiment of the present invention allows for ambulatory PCPs to send patient data into a data warehouse containing patient data from other ambulatory PCPs. In this manner, patient data may be analyzed and compared to a larger population of patients. The de-identified patient data includes an EPID 308 that may be useful in creating longitudinal reports that analyze more than one record for a particular patient. The effects of certain drugs and treatments on patient cohort groups can be analyzed and may lead to improvements in the use or composition of the drugs and treatments. In addition, an embodiment of the present invention allows for the PCP to receive cohort reports 212 based on data contained in the data warehouse. These patient cohort reports 212 include an EPID 308 for each patient. The EPID 308 may be decoded at the PCP site that created the EPID 308 and used to identify a particular patient. In this manner a PCP, by considering the information contained in the cohort report, may be able to provide improved treatment to the patient. This ability to provide useful information back to a patient level may also lead more PCPs to participate in sending patient data to a data warehouse. Having more data in the data warehouse may provide more useful information to third parties such as pharmaceutical companies, medical device companies and physicians about the effects and risks of particular treatments, while minimizing the risk of disclosing patient-identifying information to third parties. This may lead to improvements in preventative care as well as other types of medical care.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

In certain embodiments, once patient information is re-identified, the user may send the corresponding list of patients into EMR as an inquiry for further analysis, manipulation, etc. A re-identified patient record may be modified, compared, and/or otherwise manipulated by the authorized user and saved locally and/or in an EMR database or other storage. A modified record may be de-identified before is it saved, for example.

In certain embodiments, EMR updates are "pulled", "pushed", or otherwise communicated to a database, data warehouse and/or other data store on a periodic basis (e.g., nightly, weekly, etc.). In certain embodiments, changes made locally to re-identified patient records are de-identified and communicated to the EMR system and/or database for storage.

In certain embodiments, a user may search for one or more patient records within EMR by invoking a "find" dialog or search function. The user may search by the EPID, for example, and enter or select an EPID number to activate a search. The corresponding patient chart may be retrieved and displayed. Thus, a patient may be re-identified for an authorized healthcare provider who has been identified and verified.

Thus, de-identification and re-identification enable encoded and unencoded data to work in physically separated systems together. Whereas the encrypted system may host patient-level information that's HIPAA compliant and provide features that are useful from an encrypted point of view (e.g. provide data views to a larger audience, etc.), a need exists to leverage the information from the encrypted system and to re-identify the information for those audiences who are physically separated from the encrypted system but who have the authorization to view patient identifiable information. The process of re-identifying the patients is a process that occurs, for example, on the local system.

In certain embodiments, separation of de-identified and identified patient data facilitates broader analysis of patient populations without breaching individual patient security. Population-based analysis may be performed safely while maintaining patient privacy. Re-identification may occur at the local system level to allow a patient's healthcare provider to diagnose, treat and/or provide other services to the patient.

Thus, broader analysis of patient information may be allowed while at the same time respecting patient privacy. Communities of health care providers may benchmark, and compare patient populations without compromising patient privacy. At the same time, a patient's provider may re-identify patients from within the patient populations at the local level that are hosted/presented by the encrypted site. Re-identification algorithms may be stored locally at the healthcare provider level, for example. This physical separation may limit a potential risk of other providers who are viewing de-identified data on a portal from viewing patient identifiable information.

Certain embodiments allow for patient information to be shared with interested parties without compromising patient privacy. In the broader healthcare space, there will be applications where researchers, government agencies, communities of practice, may want to study patient populations but are, as of now, restricted because no good mechanism exists to work with source data providers in de-identifying and re-identifying patients. Certain embodiments facilitate such interaction. For example, decrypted information may be re-identified and then consumed by or imported into a patient's provider system within Excel, Centricity Physician Office EMR application and/or other application. Other entities, such as researchers and agencies, may view and/or manipulate the encrypted or de-identified data with reduced risk of compromising patient privacy.

Figure 5:
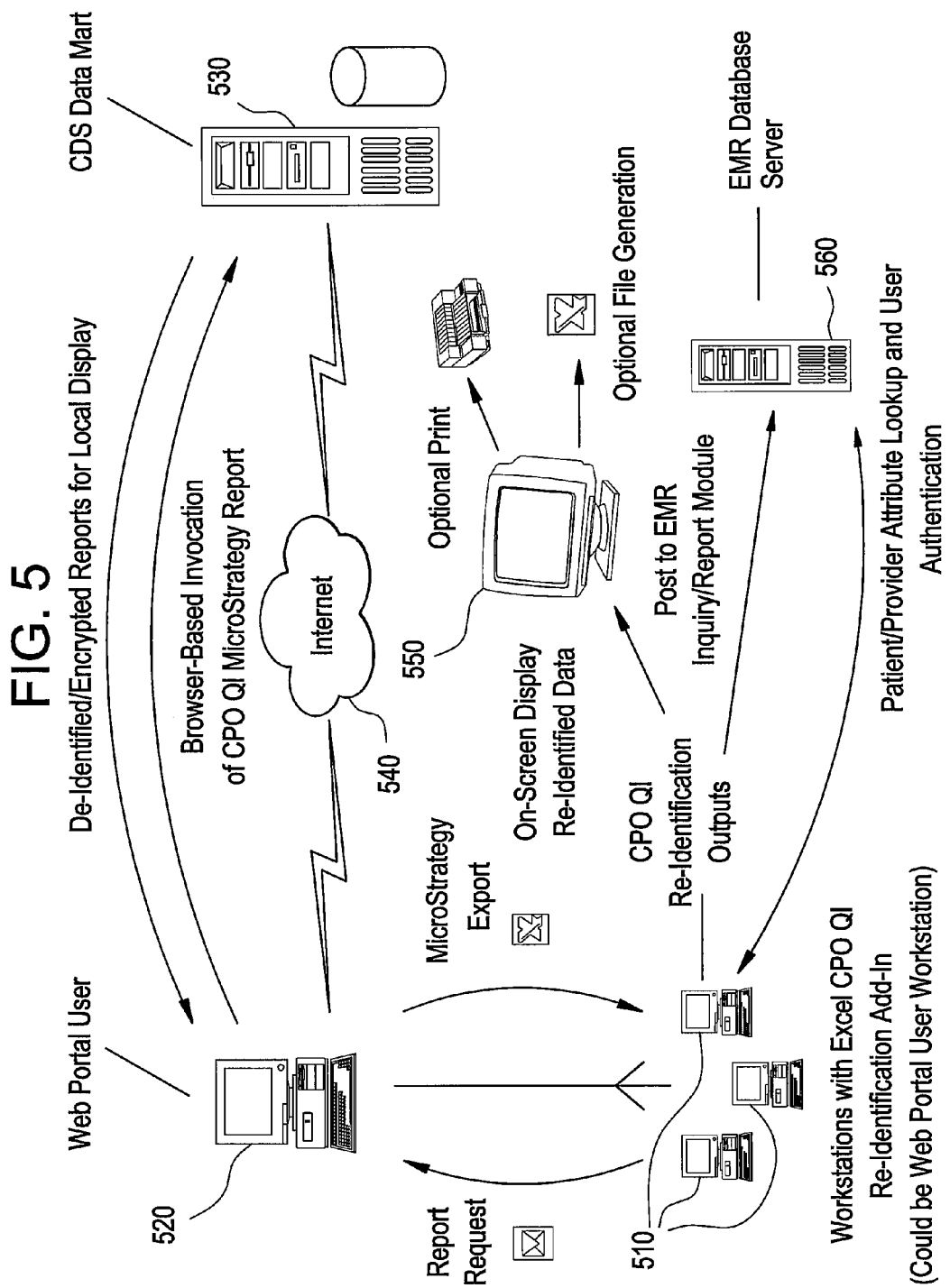
FIG. 5 illustrates a system for patient data de-identification and re-identification in accordance with an embodiment of the present invention.

FIG. 5 illustrates a system 500 for patient data de-identification and re-identification in accordance with an embodiment of the present invention. The system 500 includes one or more user workstations 510, a web portal 520, a data store 530 and a data link 540. The system 500 may also include a display 550 and/or a data server 560, for example.

The components of the system 500 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain components may be integrated in various forms and/or may be provided as software and/or other functionality on a computing device, such as a computer. Certain embodiments may omit one or more of the components of the system 500 to execute the re-identification and/or de-identification functions and communicate data between a local user and a data store.

In operation, the workstation 510 may request data via the web portal 520. For example, a user at the workstation 510 requests patient-related data via a web browser that accesses the web portal 520. The web portal 520 communicates with the data store 530 via a data link 540. For example, the web portal 520 requests the data from the data store 530, such as from an EMR data mart, via a network, such as the Internet or a private network. The data store 530 returns the requested data to the workstation 510 via the web portal 520. The data may include non-HIPAA-protected data, de-identified/encrypted patient data, re-identified patient data, and/or other data, for example.

The user workstation 510 may communicate with the display 550 to display data transmitted from the data store 530. Data may also be printed and/or used to generate a file, for example. The workstation 510 may also communicate with the data server 560 to transmit the data and/or other update, for example.

In certain embodiments, a de-identified patient report is transmitted to the workstation 510 from the data store 530 via the web portal 520 in response to a request from the workstation 510. The workstation 510 performs a re-identification of the de-identified patient data locally at the workstation 510. The re-identification may be performed via lookup of an EPID to determine a corresponding PID or other similar technique, for example. The re-identification functionality may be integrated into a document viewing/editing program, such as Microsoft Excel, Microsoft Word, and/or other software, for example. The re-identification function may access data in an external source, such as the data store 530 and/or the data server 560, to match the EPID to the PID. In certain embodiments, the EPID is replaced with the PID and/or other patient identifying information (e.g., patient name) in a document at the workstation 510.

In certain embodiments, the workstation 510 may first authenticate a privilege or right of access via the server 560, for example, before the patient data is re-identified. The workstation 510 may also lookup patient and/or provider attributes via the server 660 and/or data store 530, for example.

In certain embodiments, information in medical reports and/or other documents may be processed to normalize or "scrub" the information according to a particular lexicon and/or grammar. For example, a medical report table, such as a Logician® medical data table, may include one or more observation values from an examining physician or other medical professional. The observation value (e.g., "obs" or "obsvalue") field may be a free-format field, for example. Thus, different physicians may use different language to refer to the same condition. For example, one physician may refer to a heart attack while another may refer to an acute myocardial infarction. Terms may be "scrubbed" or parsed and associated with a numeric value and/or "standard" term for a lexicon/grammar.

For example, information in an electronic medical record or other document may be processed by a data processing system prior to storage in a data warehouse or other data collection. The information may be matched, based on one or more rules, for example, to a table or other listing of accepted terms/values. Based on the matching, the information may be replaced with the accepted term and/or value from the listing. Using the example above, if the accepted term was "acute MI", a physician's use of "heart attack" would be converted or normalized to "acute MI" and a physician's use of "acute myocardial infarction" would also be converted to "acute MI."

In certain embodiments, certain identified patient data is extracted and stored centrally in a large data warehouse. During storage, the data may be scrubbed and normalized by mapping terms to a common vocabulary and/or set of rules. For example, if one record refers to a MI and another record refers to a myocardial infarction, both are coded centrally in the database as a myocardial infarct. Thus, a search of records in the database may be executed based on the common vocabulary.

A user may execute a search using one or more terms or criteria for the search. For example, a user may request a pool of patients over the age of 55, with a history of acute myocardial infarction within the last 2 years, and certain enzyme levels, who live in the Midwest. The terms and/or criteria may already be codified in the database and/or may be codified/normalized upon entry of the search terms by the user, for example. In certain embodiments, a user may select one or more codified terms from a menu or other listing and select one or more predesigned algorithms to search for patients meeting the selected term(s). In certain embodiments, a user may codify additional term(s) and/or create additional rules/search algorithms dynamically, for example. In certain embodiments, a search system accommodates a user's query to codify language used in the query to a standard vocabulary or set of allowed terms. A search having multiple criteria may progress by applying the plurality of criteria in succession to narrow the pool of candidates. Search terms may be matched to electronic medical records and/or other entries in a data warehouse and/or other database, for example.

In certain embodiments, electronic medical record data may be centralized and codified. In certain embodiments, electronic medical record data may be distributed and/or uncodified. In certain embodiments, electronic medical record data may be codified differently in different systems. For example, a local vocabulary may be different from a centralized vocabulary and/or different local EMR systems may have different local vocabularies. In certain embodiments, a mapping may exist between a plurality of codifications to allow conversion and searching between the different codification schemes.

Terms or input by a user may be codified according to a diagnostic code such as an ICD-9 (International Classification of Diseases, Ninth Revision) code, ICD-10 code or a CPT (Current Procedure Terminology) code, for example. Alternatively and/or in addition, terms may be codified according to a proprietary terminology or coding schema. For example, an industry standard term such as "acute, upper right extremity pain" may be classified as "acute, upper right arm pain." Certain terms may be classified or replaced by commonly used terms and/or terms appropriate for a particular environment or application, for example. In certain embodiments, a user may select a term, and a master vocabulary table returns relevant terms for use in searching. In certain embodiments, one or more categories may be searched base on a clinical condition or a disease category, for example.

For example, if a user wishes to search for a "CV" (cardiovascular) issue, the user may select a number of CV conditions from a CV list. For example, a search interface may have clinical conditions listed, such as a person who had a heart attack with complications from diabetes, and the interface may have diagnostic codes listed for selection to search. A user may then search on either or both of the clinical conditions and codes by selecting conditions/codes from a flat or tiered listing or menu and/or by manually entering conditions/codes to select the clinical conditions and/or other criteria to be used to be applied to the database and search.

According to one of the examples above, a user selects the following criteria for searching: age exceeding 55, acute myocardial infarction, within a time frame of 2 years, a certain specified enzyme level or range of levels, and a geographic location of "the Midwest. A search would identify patients in the database over 55 years of age. The search would narrow that group by identifying those patients in the over 55 age group having an acute myocardial infarction within the last two years. Additionally, the search would narrow the group of patients to isolate patients over 55 who have had an acute myocardial infarction in the last two years who reside in the Midwest.

Certain embodiments provide free text searching capability within electronic medical records with automatic de-identification of patient/physician information. Additionally, certain embodiments provide multiple searching capabilities within EMRs. Searching capabilities may include searching an entire site/database for user-entered search criteria. Search capabilities may include searching a specific department, such as radiology, cardiology, pathology, etc. Search capabilities may include searching images and/or locating similar images from search results. While these capabilities are simply illustrative examples, a variety of other search capabilities may be implemented according to certain embodiments of the present invention.

In certain embodiments, a web interface can be used to access the search capabilities. Additionally, application program interfaces (APIs) can be provided for certain research capabilities. For example, APIs can be provided for finding statistical information such as a number of diagnoses for a specific disease in a specific demography, a number of diagnoses for a patient of a specific disease, etc. A search crawler may be used with a variety of information systems, such as a RIS, PACS, CVIS, LIS, etc.

Figure 6:
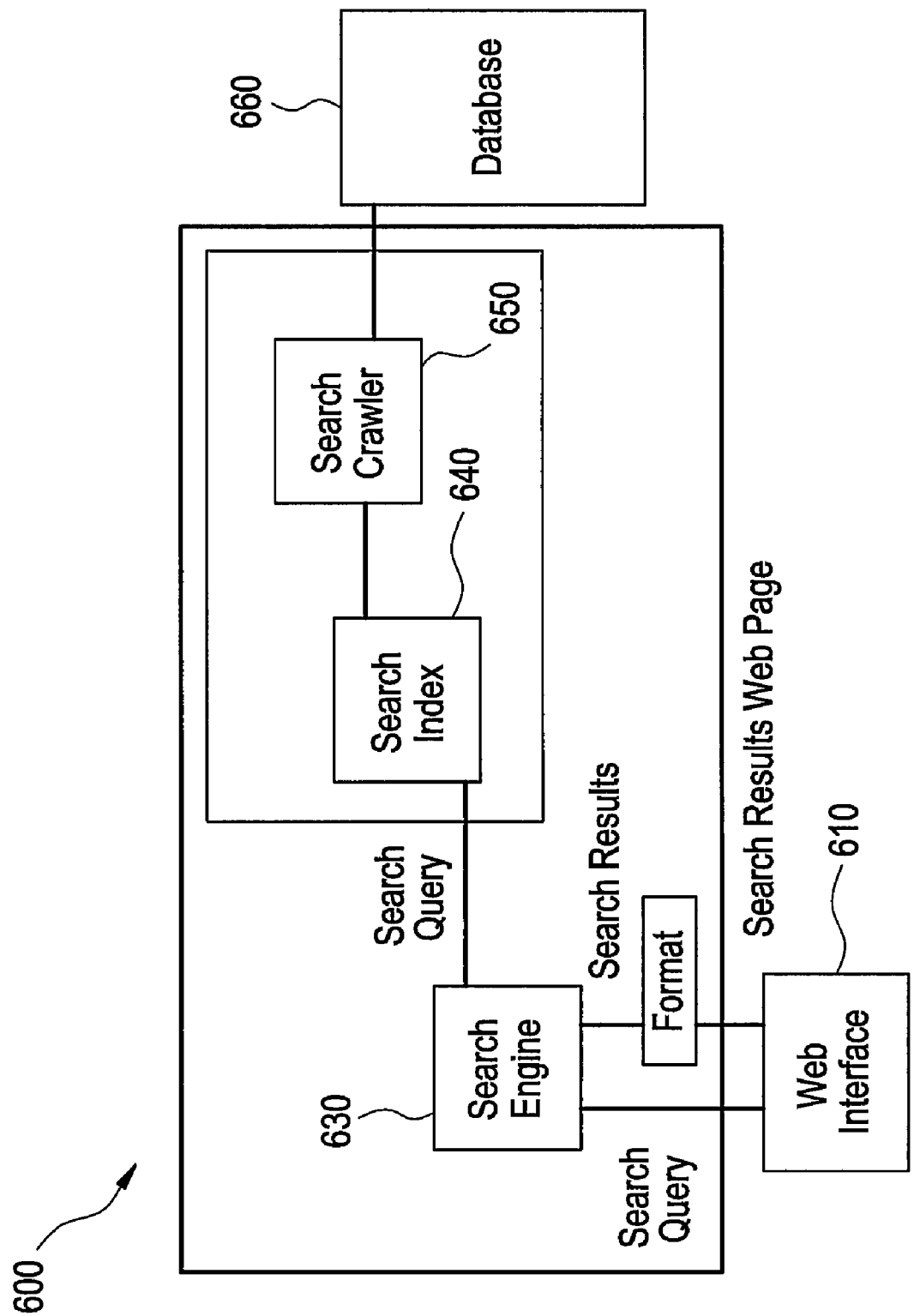
FIG. 6 illustrates an EMR search system in accordance with an embodiment of the present invention.

As shown in FIG. 6, a user may access a search using a web interface 610. One or more search criterion may be entered via the web interface 610. The interface 610 sends a search query to a search engine 630, which routes (in certain embodiments, with some processing/formatting) the search query to a search index 640. The search index 640 communicates with a search crawler 650 to convey the search query.

The search crawler 650 uses the term(s) of the search query to search a database 660, such as an EMR database. The search crawler 650 performs a free text search within the database 660, for example. A free or full text search is a search for a match of one or more specified words in the electronic documents of the EMR database 660, for example. The search may be limited by department and/or other criterion, for example. In certain embodiments, the database 660 includes multiple databases spanning multiple departments/facilities, and the crawler 650 searches one or more of these databases based on search terms/parameters.

For example, a free text search may include "CR CHEST", "CT CHEST WITH CONTRAST", "heterogeneous echotexture of the liver", "acute intracranial hemorrhage", etc. Advance searching may include, for example, "Procedure: CHEST & Modality: CT & Referring Physician: AAA & Date Range: From Jan. 2, 2007 to Jun. 6, 2007"; "Procedure: PELVIS & Modality: CT & Comments: osseous lesions & Referring Physician:"; "Procedure: CHEST & Modality: XA|Modality: CT & Comments: coronary artery bypass & Department:Cardiology|Department:Radiology"; etc.

Search results are then provided to the search index 640, which may keep a running track of search results. The search index 640 may be organized using a tree structure, for example. However, a variety of indices may be implemented. The search index 640 is used to collect, organize, parse and store search results for retrieval. Search results are then passed back to the search engine 630. The search engine 630 sends the results through a formatter 620. The formatter 620 formats the search results for display via the web interface 610. In certain embodiments, the formatter 620 de-identifies patient and/or physician identification information from the search results prior to display via the web interface 610. In certain embodiments, results can be categorized to relevance factor and/or other criterion, for example.

Figure 7:
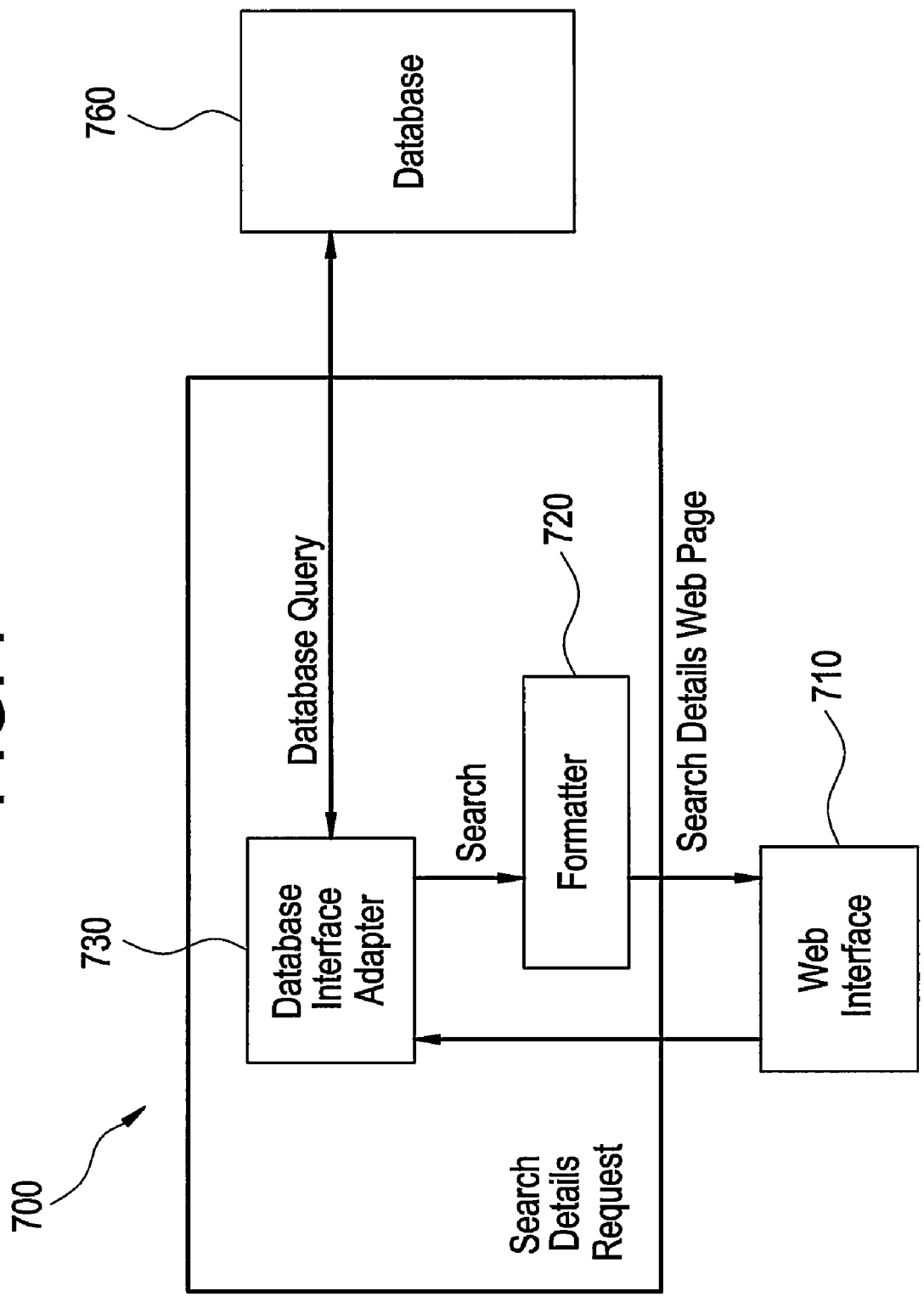
FIG. 7 illustrates a search results fetching system in accordance with an embodiment of the present invention.

As shown in FIG. 7, a user may fetch details of a search via a web interface 710 (which may be the same as or similar to the web interface 610). The web interface 710 requests data from a database interface adapter 730. The database interface adapter 730 retrieves data from the database 760 (which may be the same as or similar to the database 660). Search details are retrieved from the database 760. The database interface adapter 730 then provides the search details to a formatter 720 (which may be the same as or similar to the formatter 720). The formatter 720 formats the data so that it is appropriate for display via the web interface 710. Formatting may include helping to ensure HIPPA compliance through de-identification of patient/physician information in the search results, for example.

Components of systems 600 and 700 may be implemented in software, hardware and/or firmware and may be implemented individually and/or in a variety of combinations.

FIG. 8 illustrates a flow diagram for a method 800 for free text searching of electronic clinical data in accordance with an embodiment of the present invention. At step 810, one or more search criteria are entered. For example, a user may enter one or more search terms via an interface, such as a Web-based interface.

At step 820, a search query is formed from the one or more search terms. For example, the interface may combine terms in a format suitable for searching. At step 830, the search query is sent to the search engine for searching. For example, the interface routes the query to the search engine for searching.

At step 840, term(s) of the search query are used to search a clinical database, such as an EMR database. A search crawler, for example, may search one or more clinical databases using the search query terms(s) in a free text search. In certain embodiments, a search index tracks results of the search, for example.

At step 850, search results are formatted for output. For example, search results may be formatted for display via a web-based interface. Search results may be stored, transmitted, routed to another application, etc. In certain embodiments, search results may be filtered, organized and/or otherwise processed before output, for example. In certain embodiments, patient and/or physician identification information may be removed or anonymized from the search results prior to output. In certain embodiments, results can be categorized to relevance factor and/or other criterion, for example. At step 860, search results are output.

One or more of the steps of the method 800 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments provide quick access to relevant information about search criteria. Certain embodiments provide free text searching within electronic medical records. Certain embodiments enable automatic de-identification of patient and/or physician information. Additionally, certain embodiments provide a comprehensive search capability with various departmental information systems in a healthcare enterprise, as well as with external information systems. In certain embodiments, results can be categorized by a relevance factor, with the most relevant information available to a user more quickly. Certain embodiments provide a capability to search multiple departmental information systems and consolidate search results by relevance to search criteria and with respect to a particular patient.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A system for free text searching of electronic medical record data, said system comprising:
   an interface configured to accept search criteria and display search results;
   a search engine to accept a free text search query from the interface, the free text search query based on search criteria entered via the interface, the search engine communicating with a search crawler;
   a search crawler to search electronic medical record data based on the free text search query, said electronic medical record data including at least alphanumeric data and image data, and providing search results consolidating patient data through the free text search, the search crawler searching identified and de-identified electronic medical record data to provide consolidated search results, said search crawler to search a plurality of departmental information systems; and
   a formatter to format the search results for display via the interface, the formatter configured to consolidate results by relevance to search criteria and with respect to a particular patient, the formatter automatically de-identifying at least one of patient and physician data from the search results and providing local re-identification of at least a portion of the search results for an authorized healthcare provider user who has been identified and verified for local re-identification and access to the at least a portion of the search results at a local system,
   wherein the search results including at least one of de-identified patient data and de-identified physician data are provided to the local system and re-identified at the local system for the authorized healthcare provider user based on re-identification functionality at the authorized healthcare provider user's local system to provide physical separation of re-identified search results available to the authorized healthcare provider user and de-identified search results available to one or more additional users.

2. The system of claim 1, wherein said formatter categorizes said search results according to at least one relevance factor.

3. The system of claim 1, wherein said search crawler is configured to search a particular departmental information system.

4. The system of claim 1, wherein the interface comprises a web interface.

5. The system of claim 1, wherein said search crawler searches both alphanumeric and image data based on said search query.

6. A system of retrieving electronic medical record search results, said system comprising:
   an interface configured to accept search criteria and display search results;
   a database interface adapter to interface with an electronic medical record database to transmit and receive data, wherein the database interface adapter facilitates searching identified and de-identified electronic medical record data from a plurality of departmental information systems; and
   a formatter to format search results for display via the interface, the formatter configured to consolidate results by relevance to search criteria and with respect to a particular patient, the formatter automatically de-identifying at least one of patient and physician data from the search results and providing local re-identification of at least a portion of the search results for an authorized healthcare provider user who has been identified and verified for local re-identification and access to the at least a portion of the search results at a local system,
   wherein the search results including at least one of de-identified patient data and de-identified physician data are provided to the local system and re-identified at the local system for the authorized healthcare provider user based on re-identification functionality at the authorized healthcare provider user's local system to provide physical separation of re-identified search results available to the authorized healthcare provider user and de-identified search results available to one or more additional users.

7. The system of claim 6, wherein said interface comprises a web interface and wherein said formatter formats the search results for display via the web interface.

8. The system of claim 6, wherein said formatter categorizes said search results according to at least one relevance factor.

9. The system of claim 6, wherein said database interface adapter is configured to interface with a particular departmental information system.

10. The system of claim 6, wherein said database interface adapter is configured to interface across a plurality of departmental information systems.

11. The system of claim 6, wherein said formatter formats both alphanumeric and image search results for output.

12. A method for free text searching of electronic clinical data, said method comprising;
    receiving one or more search terms for searching of electronic clinical data;
    forming a search query based on said one or more search terms;
    crawling one or more databases associated with one or more clinical information systems including a plurality of departmental information systems to identify relevant data based on said search query, the crawling comprising searching identified and de-identified patient data in the one or more databases; and
    formatting said relevant data as search results for output, the formatting including consolidating results by relevance to search criteria and with respect to a particular patient, the formatting including automatically de-identifying at least one of patient and physician data from the search results and providing local re-identification of at least a portion of the search results for an authorized healthcare provider user who has been identified and verified for local re-identification and access to the at least a portion of the search results at a local system,
    wherein the search results including at least one of de-identified patient data and de-identified physician data are provided to the local system and re-identified at the local system for the authorized healthcare provider user based on re-identification functionality at the authorized healthcare provider user's local system to provide physical separation of re-identified search results available to the authorized healthcare provider user and de-identified search results available to one or more additional users.

13. The method of claim 12, wherein said forming step further comprises forming a search query customized for a particular departmental information system based on said one or more search terms.

14. The method of claim 12, wherein said formatting step further comprises categorizing said search results according to at least one relevance factor.

15. The method of claim 12, wherein said crawling step further comprises a targeted search customized for a particular departmental information system.

16. The method of claim 12, wherein said relevant data comprises one or more of alphanumeric and image data.

* * * * *